United States Patent [19]

Mendes et al.

[11] Patent Number: 4,996,213
[45] Date of Patent: Feb. 26, 1991

[54] DERIVATIVES OF 4-AMINO 3-CARBOXY NAPHTHYRIDINES AND THEIR PHARMACEUTICAL COMPOSITIONS

[75] Inventors: Etienne Mendes, Toulouse; Jean-Claude Vernieres; Jacques Simiaud, both of Muret; Peter E. Keane, Portet-Sur-Garonne, all of France

[73] Assignee: SANOFI, Paris, France

[21] Appl. No.: 362,104

[22] Filed: Jun. 6, 1989

[30] Foreign Application Priority Data

Jun. 9, 1988 [FR] France ................................ 88 07723

[51] Int. Cl.$^5$ ..................... A61K 31/44; C07D 471/04
[52] U.S. Cl. ..................................... 514/300; 514/183; 514/212; 540/481; 540/597; 546/122; 546/123
[58] Field of Search ................ 546/122, 123; 514/300, 514/212, 183; 540/481, 591

[56] References Cited

FOREIGN PATENT DOCUMENTS 0018735 11/1980 European Pat. Off. .
0205362 12/1986 European Pat. Off. .

OTHER PUBLICATIONS

R. M. Titkova et al., "Synthesis of 4-substituted 3-carbethoxy [carboxy]-1,5-naphthyridines, Their Properties and Biological Activity", vol. 97, No. 19, Nov. 8, 1982, p. 706, No. 162862n.

*Primary Examiner*—Robert W. Ramsuer
*Assistant Examiner*—Bernard I. Dentz
*Attorney, Agent, or Firm*—Wegner, Cantor, Mueller & Player

[57] ABSTRACT

Compounds represented by the general formula

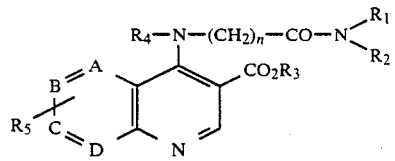

in which $R_1$ and $R_2$ are independently selected from hydrogen, $C_1$-$C_6$ alkyl, phenyl or benzyl, or $R_1$ and $R_2$ may form together with the nitrogen atom to which they are attached a $C_4$-$C_8$ saturated heterocycle, $R_3$ and $R_4$ are independently selected from hydrogen or C hd 1-$C_6$ alkyl, $R_5$ is selected from hydrogen or halogen, or $C_1$-$C_4$ alkyl, $C_1$-C hd 4 alkoxy, nitro or trifluoromethyl, n is 1, 2 or 3, and one of the symbols A, B, C or D represents N and the others represent CH, as well as the N-oxids and the the pharmaceutically acceptable acid addition salts and their salts with bases. The compounds have nervous system affecting properties.

4 Claims, No Drawings

DERIVATIVES OF 4-AMINO 3-CARBOXY NAPHTHYRIDINES AND THEIR PHARMACEUTICAL COMPOSITIONS

The present invention relates to derivatives of 4-amino 3-carboxy naphthyridine, a process for their preparation and the pharmaceutical compositions which comprise them.

The subject-matter of the invention is compounds of formula I:

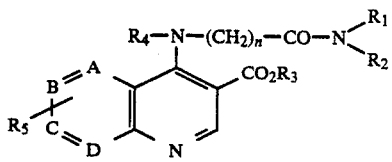

in which

R$_1$ and R$_2$ are independently selected from hydrogen, C$_1$–C$_6$ alkyl, phenyl or benzyl, or R$_1$ and R$_2$ may form together with the nitrogen atom to which they are attached a C$_4$–C$_8$ saturated heterocycle, R$_3$ and R$_4$ are independently selected from halogen or C$_1$–C$_6$ alkyl, R$_5$ is selected from hydrogen or halogen, or C$_1$–C$_4$ alkyl, C$_1$–C$_4$ alkoxy, nitro or trifluoromethyl, n is 1, 2 or 3, and one of the symbols A, B, C or D represents N and the others represent CH, as well as the N-oxides of the heterocyclic nitrogens and their addition salts with pharmaceutically acceptable acids or vith pharmaceutically acceptable bases when R$_3$ is selected from hydrogen.

The alkyl groups can be straight, branched or cyclic.

The phenyl or benzyl groups may be optionally substituted by C$_1$–C$_6$ alkyl, C$_1$–C$_6$ alkoxy, trifluromethyl or nitro groups, or by halogen atoms.

The addition salts vith acids may be formed with mineral acids such as hydrohalogen, nitric, sulfuric or phosphoric acids or with organic acids such as mono- or di- carboxylic acids, for example acetic, formic, succinic, tartaric, oxalic or aspartic acids, or with sulfonic acids such as methane sulfonic acid or benzene sulfonic acid.

The salts with the bases may be alkali or alkaline earth salts or salts with amines such as lysine, piperazine or ethanolamine.

Among the preferred compounds of the invention, mention may be made of the derivatives of 1,5-naphthyridine in which R$_3$ is methyl or ethyl, R$_4$ is hydrogen and n is 1, i.e. the derivatives of glycinamide, and more particularly those for which R$_1$ and R$_2$ are C$_3$–C$_5$ alkyl groups or R$_1$ is a C$_1$ or C$_2$ alkyl group and R$_2$ s a phenyl group as well as their salts.

In addition, the invention relates to a process for the preparation of the compounds of formula I which consists of reacting a compound of formuia II:

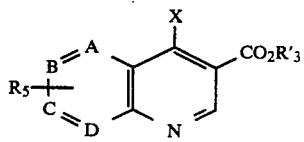

with an amine of formula R$_4$HH(CH$_2$)$_n$ CONR$_1$R$_2$ III in which R$_1$, R$_2$, R$_4$, R$_5$, n, A, B, C, D, have the same meanings as in formula I, R'$_3$ is selected from alkyl group, and X is selected from hydrogen atom or an alphatic or aromatic sulfonate group.

The substitution of the amine III can be carried out under standard conditions at a temperature between 60° C. and 150° C., preferably in the presence of a tertiary amine or a mineral base in order to bind the acid HX formed, in a solvent such as an aromatic hydrocarbon, an alcohol, or a polar aprotic solvent. (III) may be introduced into the reaction mixture in the form of a salt, with an equivalent quantity of base in order to liberate the amine in situ.

The compounds of formula I in which R$_3$=H are obtained by hydrolyzing the corresponding esters in acidic or basic medium.

The amine salts are obtained in a conventional manner by the action of at least one molar equivalent of the acid on the amines of formula I.

Some compounds of formula II are known; in particular, the 1,5-naphthyridine derivative of formula:

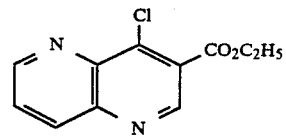

is described in Chem. Abstr. 97 162862n; it is prepared by the action of POCl$_3$ on the corresponding 3-ethoxycarbonyl 4-hydroxy 1,5-naphthyridine.

The compounds II can usually be prepared through the intermediary of the corresponding hydroxylated derivatives starting from amino pyridines according to the reaction scheme:

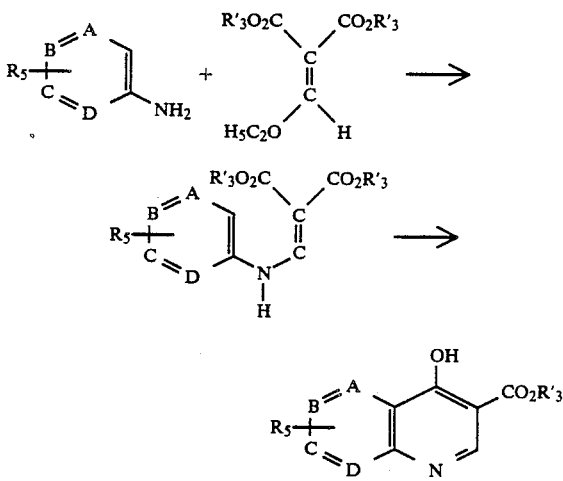

in these formulae R'$_3$, R$_5$, A, B, C, D are as in formula II.

The N-oxides of these compounds or of the corresponding chlorinated derivatives are prepared by the action of a peracid according to a known method.

These methods of preparation are described in Heterocyclic Compounds 7 p. 199–236 (1961) published by John Wiley and in Comprehensive Heterocyclic Chemistry p. 582–625 (1984) published by pergamon Press.

Some of the compounds of formula III are known; the others can be prepared by means of methods described for homologous products such as that described by R. D. Haworth et al. in J. Chem. Soc. p. 2972–2980

(1952) who prepared compounds of formula III in which $R_4=H$ through the phtalimide intermediate:

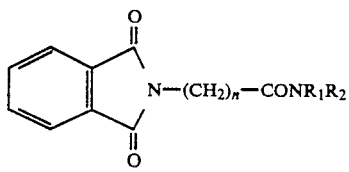

or that of G. B. BETTOLO and J. F. CAVALLA in Gazz. Chim. Ital. p. 896–907 (1954) in which the amine $R_2NH_2$ is reacted with the halogenated derivative $Cl-(CH_2)-CONR_1R_2$ obtained by the action of $NHR_1R_2$ on $ClCH_2COCl$ (in these formulae $R_1$, $R_2$ and $R_4$ are as in formula I).

The compounds of formula I and their salts have, in vitro and in vivo, a marked affinity for the central and peripheral receptors of the benzodiazepines and another object of the invention is constituted by pharmaceutical compositions which comprise as active ingredient at least one of the compounds of the invention.

Naphthyridines which are active on the central receptors of the benzodiazepines are already known, such as the 1,8-naphthyridines described in EP-A-No. 0 234 971, but the substituents of the heterocyclic ring described in this earlier document are very different from those of the products of formula I whereas other derivatives of more similar structure such as the 4-amino 1,5-naphthyridin-3-yl carboxylic acids cited in Chem. Abstr. 97 162862n have only antimicrobial activity thus, activity of a very different kind.

These compounds can be administered by the oral, rectal or parenteral routes, and the pharmaceutical compositions comprise the compounds of formula I or their salts with the excipients usually used for the preparation of tablets, capsules, granulated preparations, syrups, suppositories or injectable solutions.

It is known that the agonists of the central receptors of the benzodiazepines have anxiolytic, anticonvulsant, sedative and hyptonic activities whereas binders on the peripheral receptors may have anxiolytic cadiovascular vasodilatatory or immunomodulatroy activities. The compounds of the invention will be useful for the treatment of pathological states at daily doses of from 5 mg to 300 mg, and can be administered in one to 3 doses depending on the structure of the compounds, the age of the patient and the gravity of his condition.

The compounds of the invention may also be used as biochemical reagents.

The following examples illustrate the invention. The results of elemental analysis of the compounds prepared correspond to the accepted norm; the melting points mentioned are instant melting points. The chemical shifts in nuclear magnetic resonance spectra were determined with respect to $Si(CH_3)_4$ as internal standard; q signifies quadruplet, t triplet, m multiplet, s singlet, d doublet and (xH) the signal corresponding to x protons.

Preparation of compounds of formula II (1) Ethyl 4-chloro 1,5-naphthyridin-3-yl carboxylate (formula II: $R_3=C_2H_5$, $R_5=H$, $A=N$, $B=C=D=CH$, $X=Cl$).

0.64 ml of $POCl_3$ are introduced dropwise into a solution of 1.27 g of ethyl 4-hydroxy 1,5-naphthyridin-3-yl carboxylate prepared by using the method cited in Chem. Abst. 97 162862n, and of 0.98 ml of triethylamine in 25 ml of refluxing tetrahydrofuran, the solvent and excess $POCl_3$ are removed by distillation under reduced pressure: the residue is treated with ice-cold water and the mixture is neutralized by the addition of concentrated $NH_4OH$ before extraction of the aqueous phase with ethyl ether.

After removal of the organic solvent, a solid is obtained which is purified by chromatography on a column of silica by elution with a mixture of cyclohexane and ethyl acetate (80/20). The pure product melts at 71° C.

(2) Ethyl 4,6-dichloro 1,5-naphthyridin-3-yl carboxylate (II: $X=Cl$, $R_3=C_2H_5$, $R_5=6-Cl$, $A=N$, $B=C=D=CH$).

(a) Preparation of the naphthyridine

The mixture of 10.2 g of 5-amino 2-chloropyridine and 16 ml of ethyl ethoxymethylenemalonate is heated at 140°–150° C. The ethanol formed is distilled as it is formed. After purification by means of chromatography on a column of silica by elution with a mixture of cyclohexane and ethyl acetate (8/2) ethyl N-(2-chloro 5-pyridyl) aminoethylenealonate is recovered. m.p.=126° C. (cyclohexane; Yield: 85%.

17 g of the preceding compound are introduced into Dowtherm A prepared from 115.7 ml of diphenylether and 45 g of biphenyl; at 240° C. This solution is then heated to 245° C. and this temperature is maintained for 45 mn. The ethanol is distilled as it is formed. After being cooled to ambient temperature, the precipitate is filtered off and washed with petroleum ether. Under these conditions a mixture of ethyl(6-chloro-4-hydroxy 1,5-naphthyridin-3)-yl carboxylate and ethyl(6-chloro-4-hydroxy 1,7-naphthyridin-3)-yl carboxylate are obtained containing 95% by weight of the former.

The separation of the two isomers was carried out only at the stage of derivative II.

(b) Chlorination 12 g of the preceding mixture of isomers is introduced into 100 ml of $POCl_3$ and maintained at reflux temperature for 0.5 hour before excess $POCl_3$ is removed by distillation under reduced pressure.

The residue is then treated with ice-cold water, neutralized at a temperature between 5° and 10° C. by the addition of an aqueous solution of NaOH; the aqueous phase is then extracted twice with 150 ml of dichloromethane and the organic phases are concentrated after being dried over $MgSO_4$.

The compounds of formula II in which $X=Cl$ and $A=N$, $B=C=D=CH$ (1,5-naphthyridine; $C=N$, $A=B=D=CH$ (1,7-naphthyridine) are separated by chromatography on a column of silica by elution with a mixture of cyclohexane and ethyl acetate 95/5.

The 1,5-derivative melts at 114° C. after recrystallization from cyclohexane. $^1H$ NMR (60 MHz, $CDCl_3$): 1.10–1.30 (t, 3H) 4.10–4.60 (q, 2H) 7.40–7.50 (d, 1H) 8.05–8.30 (d, 1H) 9.15 (s, 1H), 9.40 (s, 1H).

The 1,7 derivative has a different NMR spectrum under the same conditions: 1.40–1.75 (t, 3H) 4.40–4.80 (q, 2H) 8.20 (s, 1H) 9.15 (s, 1H) 9.40 (s, 1H).

(3) ethyl(4,7-dichloro 1,8-naphthyridin-3)-yl carboxylate.

A mixture of 36 ml of $POCl_3$ and 10 g of ethyl(7-chloro-4-hydroxy 1,8-naphthyridin-3)-yl carboxylate, prepared according to the process described above in 2-a) but starting from 6-amino 2-chloro pyridine, is heated at reflux for 1 hour. The product melts at 134°–136° C. after recrystallization from cyclohexane.

(4) ethyl(4-chloro 1,6-naphthyridin-3)-yl carboxylate (II: $R_3=C_2H_5$, $R_5=H$, $A=C=D=CH$, $B=N$, $X=Cl$).

This compound is prepared by employing the method described by N. J. Weiss in Heterocyclic Compounds (1961) 7 p. 216, Elderfield, starting from ethyl(4-hydroxy-1,6-naphthyridin-3)-yl carboxylate. It melts at 72° C.

(5) 1-oxide of ethyl-4,6-dichloro 1,5-naphthyridin-3)-yl carboxylate (II: $R_3=C_2H_5$, $R_5=6$-Cl, $A=N$, $B=C=D=CH$, $X=Cl$).

10 g of ethyl(4,6-dichloro 1,5-naphthyridin-3)-yl carboxylate and 13.8 g of metachloroperbenzoic acid were stirred for 96 hours at ambient temperature in 200 ml of acetic acid. The solvent is then distilled under reduced pressure and the residue is crystallized from cold hexane. The precipitate is dissolved in dichlormethane and the solution is washed with an aqueous solution of sodium bicarbonate, then with water.

The solvent is evaporated and the residue is recrystsllized from ethanol. It melts in the range 140°–150° C.

EXAMPLE 1

Ethyl[6-chloro 4-(N,N-dipropylcarbamoylmethylamino) 1,5-naphthyridin-3]-yl carboxylate (reference: SR 25966).

Formula I: $R_1=R_2=C_3H_7$, $R_3=C_2H_5$, $R_4=H$, $R_5=6$-Cl, $A=N$, $B=C=D=CH$, $n=1$.

3.9 g of ethyl(4,6-dichloro 1,5-naphthyridin-3)-yl carboxylate, prepared as previously indicated, are refluxed with 2.7 g of 2-amino-N,N-dipropyl acetamide hydrochloride and 4.5 ml of triethylamine in 30 ml of ethanol. After removal of the solvent by distillation under reduced pressure, the residue is dissolved in 50 ml of dichloromethane and the organic phase is washed with water and dried before the solvent is removed.

The residue may be purified by chromatography on a column of silica by elution with a mixture of cyclohexane and ethyl acetate before being recrystallized from cyolohexane. M.p.=126° C. (Yield 72%). $^1$H-NMR (80 MHz, CDCl$_3$) δ ppm): 0.80–1.2 (q, 6H) 1.25–1.50 (t, 3H) 1.50–1.85 (m,4H) 3.10–3.50 (q,4H) 4.20–4.50 (q,2H) 4.80–5.00 (d,2H) 7.18–7.36 (d,1H) 7.90–8.10 (1H) 9.10 (s,1H) 10.30–10.55 (m,1H exchangeable).

EXAMPLE 2 to 27

The 1,5-naphthyridines of formula I in which $n=1$ or 2, prepared by employing the process described in example 1 are shown in the following table I.

The acid of example 22 was prepared by the action of a solution of 60 ml of 0.5N NaOH on 2.5 g of the corresponding ethyl ester for 2 hours at reflux.

The compound of Example 27 is the N-oxide of the compound of Example 26.

TABLE 1

| EX N* | SR | n | $R_1$ | $R_2$ | $R_3$ | $R_4$ | $R_5$ | F° C. | RECRYSTALLIZ. SOLVENTS |
|---|---|---|---|---|---|---|---|---|---|
| 2 | 26040 | 1 | $C_2H_5$ | $C_2H_5$ | $C_2H_5$ | H | 6-Cl | 148 | Cyclohexane |
| 3 | 26111 | 1 | $C_4H_9$ | $C_4H_9$ | $C_2H_5$ | H | 6-Cl | 109 | Cyclohexane |
| 4 | 26292 | 1 | $C_5H_{11}$ | $C_5H_{11}$ | $C_2H_5$ | H | 6-Cl | 118 | Cyclohexane |
| 5 | 26056 | 1 | $CH_3$ | H | $C_2H_5$ | H | 6-Cl | 213 | $CH_3COOC_2H_5$ |
| 6 | 26023 | 1 | $C_3H_7$ | H | $C_2H_5$ | H | 6-Cl | 218 | $CH_3COOC_2H_5$ |
| 7 | 26105 | 1 | i-$C_3H_7$ | i-$C_3H_7$ | $C_2H_5$ | H | 6-Cl | 177 | Cyclohexane |
| 8 | 26155 | 1 | i-$C_4H_9$ | i-$C_4H_9$ | $C_2H_5$ | H | 6-Cl | 141 | Cyclohexane |
| 9 | 26057 | 1 | -(CH$_2$)$_6$- | | $C_2H_5$ | H | 6-Cl | 171 | Cyclohexane |
| 10 | 26297 | 1 | $CH_3$ | $C_4H_9$ | $C_2H_5$ | H | 6-Cl | 115 | Cyclohexane |
| 11 | 26508 | 1 | $CH_3$ | sec-$C_4H_9$ | $C_2H_5$ | H | 6-Cl | 129 | Cyclohexane |
| 12 | 26081 | 1 | $CH_3$ | $C_6H_5$ | $C_2H_5$ | H | 6-Cl | 175 | Benzene |
| 13 | 26242 | 1 | $CH_3$ | (Cl-4)$C_6H_4$ | $C_2H_5$ | H | 6-Cl | 240 | $CH_3COOC_2H_5$ |
| 14 | 25998 | 1 | $C_3H_7$ | $C_3H_7$ | $C_2H_5$ | $CH_3$ | 6-Cl | 108 | Petroleum ether |
| 15 | 26130 | 1 | $C_3H_7$ | $C_3H_7$ | $CH_3$ | H | 6-Cl | 151 | Cyclohexane |
| 16 | 26216 | 1 | $C_3H_7$ | $C_3H_7$ | $C_2H_5$ | $CH_3$ | 6-$CH_3$ | 136 (maleate) | $CH_3COOC_2H_5$ |
| 17 | 26177 | 1 | $C_2H_5$ | $C_2H_5$ | $C_2H_5$ | H | 6-$CH_3$ | 118 | Cyclohexane |
| 18 | 26212 | 1 | $C_3H_7$ | $C_3H_7$ | $C_2H_5$ | H | 6-$CH_3$ | 152 | Cyclohexane |
| 19 | 26035 | 1 | $C_3H_7$ | $C_3H_7$ | $C_2H_5$ | H | 6-$OCH_3$ | 139 | Cyclohexane |
| 20 | 26099 | 1 | $C_3H_7$ | $C_3H_7$ | $C_2H_5$ | $CH_3$ | 6-$OCH_3$ | 117 (maleate) | |
| 21 | 26041 | 1 | $C_3H_7$ | $C_3H_7$ | $C_2H_5$ | H | H | 152 | Cyclohexane |
| 22 | 26236 | 1 | $C_3H_7$ | $C_3H_7$ | H | H | 6-Cl | 260 | $C_2H_5OH$ |
| 23 | 26675 | 1 | $CH_3$ | (Cl-2)$C_6H_4$ | $C_2H_5$ | H | 6-Cl | 186 | Cyclohexane |
| 24 | 26973 | 1 | $CH_3$ | (Cl-4)$C_6H_4$ | $C_2H_5$ | H | H | 178 | Cyclohexane |
| 25 | 27250 | 1 | -(CH$_2$)$_5$- | | $C_2H_5$ | H | 6-Cl | 168 | Cyclohexane |
| 26 | 26762 | 2 | $C_3H_7$ | $C_3H_7$ | $C_2H_5$ | H | 6-Cl | 98 | Cyclohexane |
| 27* | 26834 | 2 | $C_3H_7$ | $C_3H_7$ | $C_2H_5$ | H | 6-Cl | 120 | Cyclohexane |

*N-oxide

EXAMPLE 28 ethyl[6-chloro 4-(N,N-dipropylcarbamoylmethylamino; 1,7-naphthyridin-3]-yl carboxylate (SR 26224): (Formula I: $R_1=R_2=C_3H_7$; $R_3=C_2H_5$; $R_4=H$; $R_5=6$-Cl; $A=B=D=CH$; $C=N$; $n=1$).

Preparation according to the process of example 1 starting from 0.83 g of ethyl (4,6-dichloro 1,7-naphthyridin-3)-yl carboxylate, 0.65 g of 2-amino (N,N-dipropyl)acetamide hydrochloride, 0.94 ml of triethylamine and 20 ml of absolute ethanol. After purification on a column of silica (eluant:toluene and ethanol, 99/1) the residue is recrystailized from cyclohexane. M.p.=150° C. (Yield=85%). $^1$ H NMR (60 MHz CDCl$_3$) δ: 0.80–1.10 (t,6H) 1,20–1.95 (m,7H) 2.10–2.50 (q,4H) 4.30–3.65 (m,4H) 7.95 (s,1H) 9.05 (s,1H) 10.10–10.30 (m,1H).

EXAMPLE 29

Ethyl[4-(N-methyl N-4-chlorophenyl carbamoylmethylamino) 1,7-naphthyridin-3]-yl carboxylate (SR 26773) formula I: $R_1=CH_3$; $R_2=(4-Cl)C_6H_4$; $R_3=C_2H_5$; $R_4=R_5=H$; $A=B=D=CH$; $C=N$; $n=1$.

Preparation according to the process of example 1 starting from 0.69 g of ethyl (4-chloro 1,7-naphthyridin-3)-yl carboxylate described by J. C. Burray and C. R. Hauser in J. Org. Chem. p. 2008–2014 (1954), 0.66 g of 2-amino-(N-methyl N-4-chlorophenyl) acetamide hydrochloride in 10 ml of ethanol in the presence of 0.8 ml of triethylamine. The final product is isolated by chromatography on a column of silica by elution with a mixture of toluene and ethanol (95/5-v/v), and recrystallized from toluene. M.p.=242° C. (Yield: 32%).

$^1$H NMR (80 MHz, CDCl$_3$) δ: 1.2–1.5 (t,3H); 3.3 (s,3H); 4.1–4.6 (m,4H); 7.1–7.6 (m,5H); 8.3–8.5 (d,1H); 9.1 (s,1H); 9.2 (s,1H); 9.8–10.1 (m,1H).

EXAMPLE 30 to 32

1,8-naphthyridine derivatives are prepared as previously described to give:

EXAMPLE 30

(SR 26305)

formula I: $R_1=R_2=C_3H_7$, $R_3=C_2H_5$, $R_4=H$, $R_5=7$-Cl. $A=B=C=CH$, $D=N$, $n=1$.

A solution of 1.28 g of 2-amino-N,N-dipropylacetamide hydrochloride, 1.63 g of ethyl(4,7-dichloro 1,8-naphthyridin-3)-yl carboxylate, 1.85 ml of triethylamine in 30 ml of ethanol are refluxed for 2 hours.

The volatile products are removed under reduced pressure and the final product is extracted from the residue by cyclohexane in a Soxhlet in 75% yield. M.p.=151° C. $^1$H NMR (60 MHz, CDCl$_3$): 0.70–1.10 (t,6H) 1.30–1.90 (s,7H) 3.00–3.60 (q,4H) 4.20–4.70 (m,4H) 7.00–7.20 (d,1H) 8.30–8.50 (d,1H) 9.0 (s,1H) 10.5 (m,1H).

EXAMPLE 31

(SR 26285)

formula I: $R_1=R_2=C_3H_7$, $R_3=C_2H_5$, $R_4=H$, $R_5=7$-CH$_3$, $A=B=C=CH$, $D=N$, $n=1$.

M.p.=162° C. (recrystallization from ethyl acetate)

$^1$H NMR (60 HHz, CDCl$_3$) δ: 0.70–1.05 (m,6H) 1.30–1.90 (m,7H) 2.60 (m,3H) 3.0–3.55 (q,4H) 4.20–4.60 (m,4H) 6.95–7.10 (d,1H) 8.30–8.50 (d,1H) 9.10 (s,1H) 10.10–10.40 (m,1H).

EXAMPLE 32

(SR 26323)

Formula I: $R_1=CH_3$, $R_2=(4-Cl)C_6H_4$, $R_3=C_2H_5$, $R_4=H$, $R_5=7$-Cl, $A=B=C=CH$, $D=N$, $n=1$.

M.p.=174° C. (recrystallization from acetonitrile).

EXAMPLE 33

Ethyl[4-(M-methyl N-4-chlorophenylcarbamoylmethylamino) 1,6-naphthyridin-3]-yl carboxylate (SR 26625) (Formula I: $R_1=CH_3$; $R_2=(4-Cl)C_6H_4$; $R_3=C_2H_5$; $R_4=R_5=H$; $A=C=D=CH$; $B=N$; $n=1$).

M.p.=232° C. after recrystallization from ethanol.

$^1$H NMR (80 MHz, CDCl$_3$; δ: 1.20–1.60 (t,3H); 3.4 (s,3H); 4.1–4.6 (m,4H); 7.1–7.7 (m,5H); 8.4–8.6 (d,1H); 9–9.2 (d,2H); 10.4–10.7 (m,1H).

EXAMPLE 34

Ethyl[4-(N,N-dipropylcarbamoylmethylamino) 1,6-naphthyridin-3]-yl carboxylate (SR 25874) (formula I: $R_1=R_2=C_3H_7$ ; $R_3=C_2H_5$; $R_4=R_5=H$; $A=C=D=CH$; $B=N$).

M.p.=145° after recrystallization from cyclohexane.

EXAMPLE 35

Tablets with the product of example 15.

The tablets are prepared according to the usual techniques with 30 mg of SR 26130 and as excipients lactose (80 mg), maize starch (4 mg), magnesium stearate (1 mg) and polyvinylpyrrolidone (2 mg).

EXAMPLE 36

Capsules with the product of example 1.

25 mg of SR 25966 are introduced into gelatin capsules of size 1 compacted with 10 mg of cellulose, 30 mg of lactose, 5 mg of talc, 5 mg of sodium carboxymethyl starch and 1 mg of magnesium stearate.

The compounds of the preceding examples have little toxicity: as an indication, it may be pointed out that the LD$_{50}$ in the mouse is 1800 mg/kg for the compound of example 1 administered by the oral route.

Their affinity in vitro for the central and peripheral benzodiazepine receptors has also been determined as has, for some of them, their anxiolytic, hypnotic and anticonvulsant activity in vivo.

(a) Affinity for the central benzodiazepine receptors in vitro:

A method similar to that described by Braestrup and Squires in Proc. Nat. Acad. USA 74 (9) p. 3805–3809 (1977) has been used but incubation waa carried out at 4° C. for 90 mn in the presence of 1.5 mM $^3$H-flunitrazepam.

The results are shown in Table II.

TABLE II

| EXAMPLE | IC$_{50}$ (nM) | EXAMPLE | IC$_{50}$ (nM) |
| --- | --- | --- | --- |
| 1 | 45 | 18 | 20 |
| 2 | 182 | 19 | 143 |
| 4 | 1520 | 20 | 3280 |
| 8 | 172 | 21 | 396 |
| 10 | 133 | 22 | 3.6 |
| 12 | 27 | 23 | 22 |
| 13 | 59 | 24 | 738 |
| 14 | 2750 | 26 | 190 |
| 15 | 18 | 27 | 84 |
| 16 | 674 | 33 | 858 |
| 17 | 186 | diazepam | 11 |
|  |  | Chlordiazepoxide | 654 |

(b) Affinity for the peripheral benzodiazepine receptors in vitro:

The IC$_{50}$ is the concentration of the substance tested inhibiting 50% of the specific binding of PK 11195, a known binder of the peripheral type receptors; the tritiated form of this compound, N-1-methylpropyl (2-chloro-1-phenyl) 3-isoquinolyl carboxamide is sold by the CEA (France). The method used is similar to that of J. Benavides et al. described in Brain Res. Bull. 60–77 (1984).

The results obtained are shown in table III which follows:

TABLE III

| EXAMPLE | IC$_{50}$ (nM) | EXAMPLE | IC$_{50}$ (nM) |
| --- | --- | --- | --- |
| 1 | 26 | 20 | 276 |
| 2 | 270 | 21 | 58 |
| 4 | 18 | 22 | 223 |
| 8 | 18 | 23 | 0.26 |
| 10 | 55 | 24 | 2.6 |
| 12 | 9.2 |  |  |
| 13 | 0.53 |  |  |
| 14 | 213 | 26 | 35 |

TABLE III-continued

| EXAMPLE | IC$_{50}$ (nM) | EXAMPLE | IC$_{50}$ (nM) |
|---------|----------------|---------|----------------|
| 15 | 12 | 27 | 282 |
| 16 | 393 | 28 | 622 |
| 17 | 114 | 29 | 62 |
| 18 | 33 | 32 | 10 |
| 19 | 98 | 33 | 107 |

(C) Anticonvulsant activity

The extent to which the products protect animals against convulsive crises triggered by the administration of pentetrazole was determined according to the method described by Everett and Richards in J. Pharm. Exp. Ther. p. 402–407 (1977).

The compounds to be tested were administered by the oral route to groups of 10 mice 30 minutes before the subcutaneous injection of 125 mg/kg of pentetrazole. The number of animals with no tonic crises during the 30 minutes following the administration of the convulsive agent is noted and the effective dose 50 is determined, i.e. the dose at which 50% of the animals are protected.

The results as well as those obtained with known anticonvulsants are shown in table IV; the 95% confidence limits were calculated by applying the method of Finney.

TABLE IV

| EXAMPLE | ED$_{50}$ (mg/kg) (confidence interval) |
|---------|------------------------------------------|
| 1 | 11 (7–16) |
| 19 | 22 (15–19) |
| 15 | 11 (19–43) |
| chlordiazepoxide | 7 |
| phenobarbital | 10 |
| meprobamate | 36 |

(d) Anxiolytic activity

The method of R. J. Stephens described in Brit. J. Pharmacol. p. 145P (1973) was applied.

It is known that anxiolytics diminish the inhibition of the taking of food observed in the mouse placed in a strange environment snd offered unknovn food.

The compound of example 19, administered by the oral route at a dose of 32 mg/kg, increases food consumption by 130% whereas, under the same conditions, it is increased by only 73% with chlordiazepoxide st a dose of 16 mg/kg, by 80% with diazepam at a dose of 4 mg/kg and by 95% with meprobamate at 60 mg/kg.

(e) Hypnotic activity in vivo

The activity was studied by applying the method of Janssen deacribed in J. Med. Pharm. Chem p. 281 (1959). In this way it was determined that the ED$_{50}$ the compound of example 1 was 8 mg/kg by the I.V. route, whereas that of sodium thiopental is 17 mg/kg.

We claim:

1. A compound of formula I:

$$R_4-N-(CH_2)_n-CO-N\begin{matrix}R_1\\R_2\end{matrix}$$

(with pyridine ring bearing A, B, C, D positions, $R_5$ substituent, and $CO_2R_3$ group) I in which $R_1$ and $R_2$ are independently selected from hydrogen, $C_1-C_6$ alkyl, phenyl optionally substituted by at least one group selected from the class consisting of $C_{1-6}$ alkyl, $C_{1-6}$ alkoxy, trifluoromethyl, nitro, and halogen, or benzyl optionally substituted by at least one group selected from the class consisting of $C_{1-6}$ alkyl, $C_{1-6}$ alkoxy, trifluoromethyl, nitro, or halogen, or $R_1$ and $R_2$ may form together with the nitrogen atom to which they are attached a $C_4-C_8$ saturated heterocycle, $R_3$ and $R_4$ are independently selected from hydrogen or $C_1-C_6$ alkyl, $R_5$ is selected from hydrogen or halogen, or $C_1-C_4$ alkyl, $C_1-C_4$ alkoxy, nitro or trifluoromethyl, n is 1, 2 or 3, and one of the symbols A, B, C or D represents N and the others represent CH, as well as the N-oxides of the heterocyclic nitrogens and their addition salts with pharmaceutically acceptable acids and bases.

2. A compound according to claim 1 in which A of Formula I represents N and B, C, D each represents CH.

3. A compound according to claim 1 in which $R_4$ represents H and N is 1 in Formula I.

4. Pharmaceutical composition containing as active ingredient a compound according to claim 1 and an excipient.

* * * * *